United States Patent [19]

Failli

[11] Patent Number: 4,960,902

[45] Date of Patent: Oct. 2, 1990

[54] TRIFLUOROMETHOXY SUBSTITUTED 1,3,4,9-TETRAHYDROPYRANO-(3,4-b)IN-DOLE-1-ACETIC ACIDS

[75] Inventor: Amedeo A. Failli, Princeton Junction, N.J.

[73] Assignee: American Home Products Corporation, New York, N.Y.

[21] Appl. No.: 234,790

[22] Filed: Aug. 19, 1988

[51] Int. Cl.$^5$ .................................. C07D 491/052
[52] U.S. Cl. .............................................. 548/432
[58] Field of Search ........................ 514/411; 548/432

[56] References Cited

U.S. PATENT DOCUMENTS

| | | | |
|---|---|---|---|
| 3,939,178 | 2/1976 | Demerson et al. | 548/432 |
| 4,076,831 | 2/1978 | Demerson et al. | 548/432 |
| 4,810,699 | 3/1989 | Sabatucci et al. | 548/432 |

OTHER PUBLICATIONS

W. A. Sheppard, J. Am. Chem. Soc., 85, 1314–1318 (1963).
P. N. Craig, J. Med. Chem., 14, 680–684 (1971).
W. A. Sheppard, J. Am. Chem. Soc., 83, 4860–4861 (1961).

*Primary Examiner*—Mary E. Ceperley
*Attorney, Agent, or Firm*—Walter Patton

[57] ABSTRACT

Indole derivatives characterized by having a 1,3,4,9-tetrahydropyrano[3,4-b]indole-1-acetic acid nucleus bearing a trifluoromethoxy substituent in the 5-, 6-, 7-, or 8-position, and methods for their preparation and use, are disclosed. The derivatives are useful anti-inflammatory and analgesic agents.

1 Claim, No Drawings

TRIFLUOROMETHOXY SUBSTITUTED 1,3,4,9-TETRAHYDROPYRANO-(3,4-b)INDOLE-1-ACETIC ACIDS

BACKGROUND OF THE INVENTION a. Field of Invention

This invention relates to novel indole derivatives, and to the processes for their preparation and use.

Notwithstanding the advances made during the last four decades in the development of agents for the treatment of inflammatory conditions and for analgesic purposes in conditions which require relief from pain in a mammal, there still remains a need for effective agents without the side effects associated with the therapeutic agents presently used for these purposes.

More specifically, this invention relates to tricyclic acetic acid derivatives in which the tricyclic portion thereof is characterized by having an indole portion fused to a pyrano ring. Still more specifically, the compounds of this invention are characterized as derivatives of the following tricyclic acetic acid system:

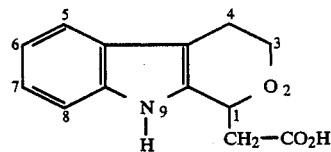

1,3,4,9-tetrahydropyrano[3,4-b]indole-1-acetic acid in which the carbon at the 1-position is further substituted with an alkyl group and the 5-, 6-, 7-, or 8-positions is further substituted with a trifluoromethoxy group.

The indole derivatives of this invention have been found to exhibit useful pharmacodynamic properties without eliciting undesirable side effects. Notable attributes of this effect are anti-inflammatory and analgesic activities.

b. Prior Art

The closest prior art to the present invention is:

Demerson et al, U.S. Pat. No. 3,939,178. Demerson et al disclosed 1,3,4,9-tetrahydropyrano[3,4-b]indoles and 1,3,4,9-tetrahydrothiopyrano[3,4-b]indoles having analgesic and anti-inflammatory activity but not with the substituents of the present invention.

SUMMARY OF THE INVENTION

The compounds of this invention are represented by formula (I)

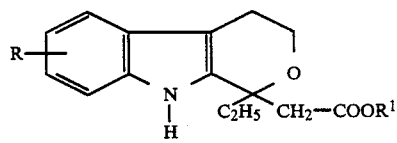

wherein R is trifluoromethoxy; $R^1$ is hydrogen or 3-oxo-1-isobenzofuranyl, and the pharmaceutically acceptable salts thereof, when $R^1$ is hydrogen.

The preferred compounds of the present invention are designated 1-ethyl-1,3,4,9-tetrahydro-7-(trifluoromethoxy)-pyrano[3,4-b]indole-1-acetic acid;

1-ethyl-1,3,4,9-tetrahydro-5-(trifluoromethoxy)-pyrano[3,4-b]indole-1-acetic acid;

1-ethyl-1,3,4,9-tetrahydro-8-(trifluoromethoxy)-pyrano[3,4-b]indole-1-acetic acid;

1-ethyl-1,3,4,9-tetrahydro-6-(trifluoromethoxy)-pyrano[3,4-b]indole-1-acetic acid and the pharmaceutically acceptable salts thereof.

Also preferred is the ester designated 1-ethyl-1,3,4,9-tetrahydro-7-(trifluoromethoxy)-pyrano[3,4-b]indole-1-acetic acid 3-oxo-1-isobenzofuranyl ester.

The indole derivatives of this invention of formula (I) are prepared by the following processes.

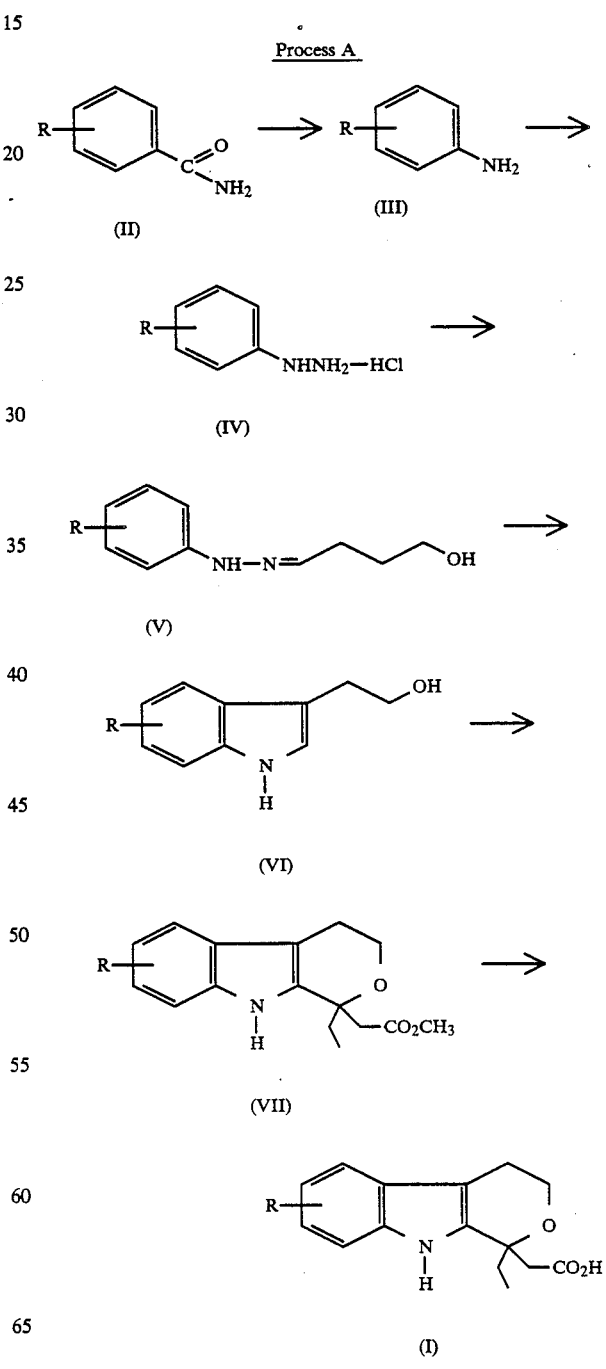

wherein R is trifluoromethoxy.

Process B

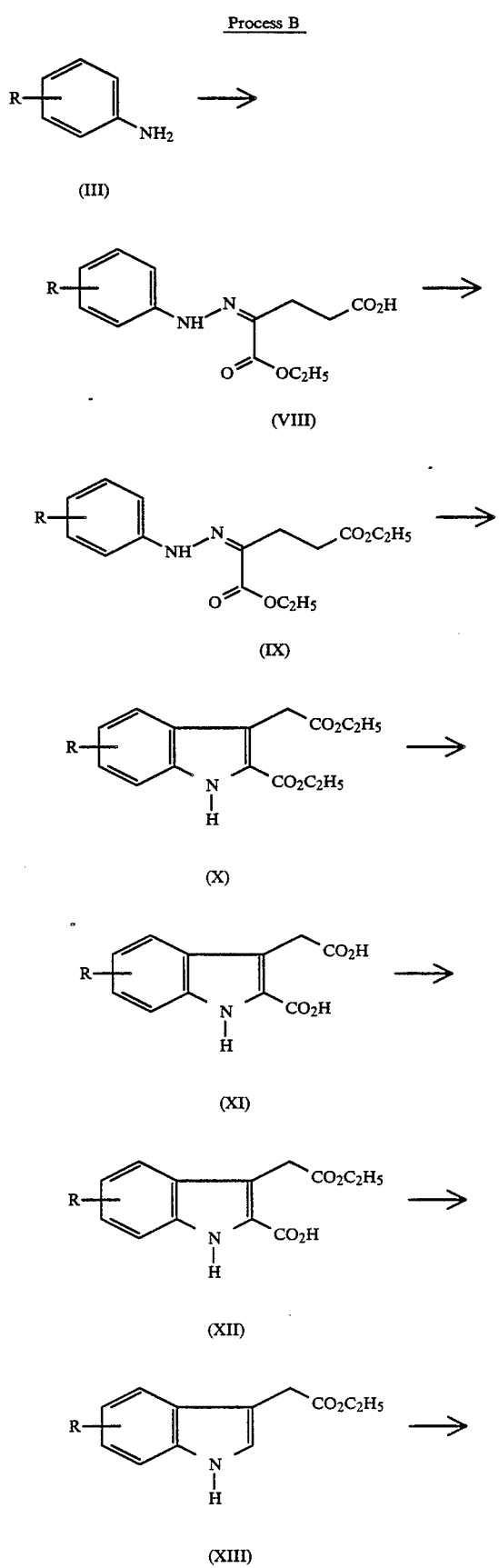

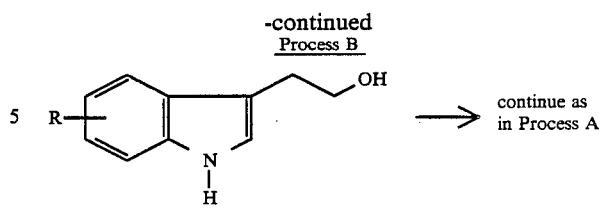

wherein R is trifluoromethoxy.

DETAILED DESCRIPTION OF THE INVENTION

The term "lower alkyl" as used herein represents straight chain alkyl radicals containing 1 to 4 carbon atoms and branched chain alkyl radicals containing three to four carbon atoms and includes methyl, ethyl, propyl, isopropyl, butyl, isobutyl and the like.

The term "halogen" as used herein includes fluorine, chlorine, bromine and iodine.

The compounds of formula (I) form salts with suitable pharmaceutically acceptable inorganic and organic bases. These derived salts possess the same activities as the parent acid and are included within the scope of this invention. The acid of formula (I) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. The preferred salt is the sodium salt. Suitable organic bases include the following amines; lower mono-, di- and tri-alkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; amino sugars, such as glucosamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methyl-pyridinium, N-methyl-N-(2-hydroxyethyl)-morpholinium, N,N-dimethyl-morpholinium, N-methyl-N-(2-hydroxyethyl)morpholinium, N,N-dimethyl-piperidinium salts, which are characterized by good water-solubility. In principle, however, there can be used all the ammonium salts which are physiologically compatible.

The transformations to the salts can be carried out by a variety of methods known in the art. For example, in the case of salts of inorganic bases, it is preferred to dissolve the acid of formula (I) in water containing at least one equivalent amount of a hydroxide, carbonate, or bicarbonate. Advantageously, the reaction is performed in a water-miscible organic solvent inert to the reaction conditions, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid salt if that form is desired.

To produce an amine salt, the acid of formula (I) is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

Also included in this invention are the optical isomers of the compounds of formula (I) which result from asymmetric centers, contained therein e.g. 1-carbon. Such isomers can be obtained in substantially pure form by classical separation techniques and by stereochemically controlled syntheses. Included is the specific case of the resolution of 1-ethyl-1,3,4,9-tetrahydropyrano[3,4-b]indole-1-acetic acids into their optical isomers by separation of the corresponding [(1S)-endo]-1,7,7-trimethyl-bicyclo[2.2.1]heptan-2-yl esters followed by basic hydrolysis.

ANTI-INFLAMMATORY ACTIVITY

The useful anti-inflammatory activities of the pyranoindole acetic acid derivatives of formula (I) are demonstrated in standard pharmacologic tests, for example, the test designated: Preventative Adjuvant Edema The objective of this test is to determine the ability of test drugs to exhibit an acute anti-inflammatory effect in rats. This test is a primary screen for anti-inflammatory drugs.

Species:

Male Sprague Dawley rats (180–200 g) are used. The animals have free access to water but food is withdrawn 18 hours before testing.

Drug Preparations and Administration:

Freund's complete adjuvant is prepared by suspending 5 mg of killed and dried Mycobacterium butyricum (Difco) in 1 mL mineral oil. The test compounds are dissolved, or suspended in 0.5% Tween 80 in distilled water according to their solubility. For primary screening all drugs are administered by gastric gavage at the arbitrary dosage of 25 mg/kg, p.o. in a volume of 0.5 mL/100 g body weight to groups of 10 animals.

Methodological Details:

The method is essentially that described by Wax et al, J. Pharmacol. Exp. Ther., 192, 166–171 (1975). Groups of rats are injected intradermally in the left hind paw with 0.1 mL of Freund's complete adjuvant. The test compound or vehicle is administered immediately before the adjuvant, 24 hours and 48 hours after the adjuvant (days 0, 1 and 2). The injected hind paw volume is measured before the injection of adjuvant and 24 hrs. after the last drug administration (day 3) by means of a plethysmometer (Buxco Electronics Inc.). The difference between the hind paw volume on day 0 and day 3 represents the edema volume. Etodolac (25 mg/kg, p.o.) is included as a positive control.

Presentation of Results:

The mean edema volume (expressed as mL ± SEM) is calculated for each group and the percentage protection conferred by the drug is calculated:

$$\% \text{ protection} = \frac{(c - t) \, 100}{c}$$

where c is the mean edema volume for the vehicle-treated (0.5% Tween 80 in distilled water) controls and t is the mean edema volume for the drug treated group.

ANALGESIC ACTIVITY

A further test used to determine the utility of the compounds of the present invention is designated: Drug Effects on Phenylbenzoquinone-induced Writhing in Mice The objective of this test is to determine the ability of test drugs to inhibit the nociceptive (pain) response of mice injected with a chemical irritant. This test is a primary screen for both peripheral and centrally acting analgesic drugs.

Species:

Male Swiss albino mice (15–25 g). The animals are fasted for 18 hours prior to use but have free access to water.

Drug Preparation and Administration:

Drugs are dissolved or suspended according to their solubility in 0.5% Tween 80 in distilled water. They are administered by gastric gavage in a volume of 5 mL/kg. For primary screening all drugs are administered at the arbitary dosage of 10 mg/kg, p.o. to a group of 10 mice.

Methodological Details:

A modification of the method of Siegmund et al, Proc. Soc. Exp. Biol. Med., 95, 729–731 (1957) is used. Groups of 5 mice are dosed with the test compound or vehicle control. Sixty minutes later the animals are injected i.p. with 0.3 mL/20 g body weight of a 0.02% solution of phenylbenzoquinone (PBQ; 2-phenyl-1,4-benzoquinone) and placed in individual observation boxes. The number of writhing or abdominal squirming movements made by each mouse during the following 15 min. period is counted. The experiment is repeated with another group of 5 mice and the mean number of writhes per mouse for a group of 10 mice is calculated.

Presentation of Results:

Drug treated and vehicle-treated control groups are compared and the percentage protection conferred by the drug is calculated:

$$\text{Percentage protection} = \frac{(c - t) \, 100}{c}$$

where c = mean number of writhes in the control group
where t = mean number of writhes in the test drug group

ANTI-INFLAMMATORY EFFECT AGAINST ESTABLISHED EDEMA IN ADJUVANT ARTHRITIC RATS

An additional test used to determine the utility of the compounds of the present invention is designated: Curvative Adjuvant Arthritis.

The objective of this test is to evaluate the ability of drugs to decrease edema in rats with established adjuvant arthritis in order to characterize further the anti-inflammatory activity of the compounds of the present invention.

Species:

Male inbred Wistar Lewis rats with an initial body weight of 180–200 g were used. The animals had free access to food and water throughout the test.

Drug Preparations and Administration:

Freund's Complete Adjuvant (FCA) was prepared by suspending 5 mg killed and dried *Mycobacterium butyricum* (Difco) in 1 mL mineral oil. The test compounds were dissolved, or suspended with a few drops of Tween 80, in distilled water according to their solubility. They were administered by gastric gavage in a volume of 0.5 mL/100 g body weight to groups of 10 animals at doses of 3 mg/kg/day p.o.

Methodological Details:

Arthritis was induced in rats by intradermal injection of 0.1 mL FCA in the distal third of the tail (day 0). The volume of both hind paws were measured and body weight recorded at that time. On day 16 after FCA injection the volume of both hind paws were again measured. Only rats with consistent and well established arthritis were selected for further experimentation (i.e. an increase in volume of between 1.0 and 2.5 mLs for both hind paws and a difference between left and right hind paws no greater than 25%). Such animals were distributed into groups of 10 so that there was no significant difference in mean hind paw volume between groups. Mean body weight for each group was recorded. Drug or vehicle treatment was initiated on day 16. Animals were dosed daily from day 16 to day 25 (i.e. a total of 9 doses). The volume of both hind paws and the body weight of the animal was recorded 2 hours after the last drug administration. Vehicle treated arthritic animals acted as a vehicle-treated control group and animals treated with etodolac (3 mg/kg po) acted as a positive control group.

Presentation of Results:

The results are expressed as a change in hind paw volume (mean of both hind paws) and a change in body weight from day 16 to day 25. The $ED_{50}$, or dose which causes such an effect in 50% animals, is calculated by probit analysis.

Typical results obtained for the compounds of the present invention in the aforementioned tests are as follows:

TABLE I

| Drug | Preventative Adjuvant Edema* | Phenylquinone Writhing in Mice* |
|---|---|---|
| 1-ethyl-1,3,4,9-tetrahydro-7-(trifluoromethoxy)pyrano-[3,4-b]indole-1-acetic acid | 88 (25) | 47 (10) 24 |
| etodolac | 68 (25) | 168 |

*The numbers quoted are either percent inhibition at the dose in mg/kg given in parentheses or the $ED_{50}$ in mg/kg.

TABLE II

| | Curative Adjuvant Arthritis | | | |
|---|---|---|---|---|
| Drug | Dose mg/kg/day p.o. | Injected Paw Edema (mL) | Non-Injected Paw Edema (mL) | Body Weight Change (g) |
| Control | — | +1.82 | +2.46 | −6 |
| 1-ethyl-1,3,4,9-tetrahydro-7-(trifluoromethoxy)pyrano-[3,4-b]indole-1-acetic acid | 0.3 | +0.53 | +1.21 | +2 |
| | 1 | −0.18 | −0.35 | +2 |
| | 3 | −0.60 | +0.11 | +20 |
| etodolac | 0.3 | +1.12 | +1.86 | −3 |
| | 1 | +0.40 | +1.14 | −9 |
| | 3 | −0.28 | +0.51 | +10 |

In curative adjuvant arthritis, 1-ethyl-1,3,4,9-tetrahydro-7-(trifluoromethoxy)pyrano-[3,4-b]indole-1-acetic acid at 1 mg/kg/day produced an anti-inflammatory effect intermediate between that produced by 1 and 3 mg/kg etodolac. Accordingly, said compound is approximately 2-fold more potent than etodolac (Table II). In addition, animals treated with the highest dose of 1-ethyl-1,3,4,9-tetrahydro-7-(trifluoromethoxy)pyrano-[3,4-b]indole-1-acetic acid (3 mg/kg/day) appeared healthy as assessed by body weight gain.

The lack of side effects associated with the compounds of this invention are demonstrated by standard acute toxicity tests as described by R. A. Turner in "Screening Methods in Pharmacology," Academic Press, New York and London, 1965, pp. 152–163, and by prolonged administration of the compound to warm-blooded animals.

When the compounds of this invention are employed as anti-inflammatory and analgesic agents in warm-blooded animals, they are administered orally, alone or in dosage forms, i.e., capsules or tablets, combined with pharmacologically acceptable excipients, such as starch, milk sugar and so forth, or they are administered orally in the form of solutions in suitable vehicles such as vegetable oils or water. The compounds of this invention may be administered orally in sustained release dosage form or transdermally in ointments or patches. The compounds of this invention may also be administered in the form of suppositories.

The dosage of the compounds of formula (I) of this invention will vary with the particular compound chosen and form of administration. Furthermore, it will vary with the particular host under treatment. Generally, the compounds of this invention are administered at a concentration level that affords efficacy without any deleterious side effects. These effective anti-inflammatory and analgesic concentration levels are usually obtained within a therapeutic range of 1.0 μg to 500 mg/kg per day, with a preferred range of 1.0 μg to 100 mg/kg per day. The preferred anti-inflammatory and analgesic dose range is 20 μg to 20 mg/kg/day.

The compounds of this invention may be administered in conjunction with nonsteroidal anti-inflammatory drugs such as ibuprofen and aspirin, and/or with opiate analgesics such as codeine, oxycodone and morphine together with the usual doses of caffeine, or in combination with antihistamines, decongestants, and antitussives. When used in combination with other drugs, the dosage of the compounds of the present invention is adjusted accordingly.

The following examples further illustrate this invention.

EXAMPLE 1

1-Ethyl-1,3,4,9-tetrahydro-7-(trifluoromethoxy)-pyrano[3,4-b]indole-1-acetic Acid and 1-Ethyl-1,3,4,9-tetrahydro-5-(trifluoromethoxy)-pyrano[3,4-b]indole-1-acetic Acid Process A Step (1) Preparation of m-Trifluoromethoxyaniline According to the procedure of J. S. Buck et al, Org. Synth. II, 44 (1943), m-trifluoromethoxybenzamide (4 g, 19.5 mmol) was added portionwise to a cold, stirred mixture of 5% NaOCl (28.26 mL) and 50% NaOH (1.41 mL). The mixture was gently warmed until it became homogeneous (about 55° C.) and then kept at 70° C. (internal temperature) for 2 hours. At this point additional 50% NaOH was added (7.7 mL) and the mixture was heated at 80° C. for 3 hours. Upon cooling it was extracted with ether (3X); the extracts were washed with brine and dried (MgSO$_4$). The ether was distilled off at atmospheric pressure to avoid losses of the somewhat volatile amine. The residual brown oil, obtained in quantitative yield, was pure enough to be used as such in the next step. If needed, however, it can be further purified by distillation, b.p. 85°-86° C. at 20 mm Hg (W. A. Sheppard, J. Org. Chem., 29, 1 (1964): 89° C./20 mm or 70° C./7 mm).

NMR (CDCl$_3$, 400 MHz): δ3.9 (broad s, NH$_2$), 6.51 (s, 1H, Ar-H), 6.58 (mm, 2H, Ar-H), 7.13 (t, 1H, J=8 Hz, Ar-H).

Step (2) Preparation of m-Trifluoromethoxyphenylhydrazine Hydrochloride

According to the procedure of I. T. Barnish et al, J. Chem. Soc. Perkin I, 215 (1974), m-trifluoromethoxyaniline (54.71 mmol) was added to cold, concentrated HCl (142 mL) and the suspension diazotized at −2° C. (internal temperature) by adding a solution of NaNO$_2$ (4.15 g, 1.1 equivalents) in water (35.6 mL). After 15-30 minutes, the mixture was treated with a solution of urea (2.5 g) in water (8.5 mL). It was then cooled to −4° C. (internal temperature) and reduced by rapidly adding a solution of tin (II) chloride dihydrate (15.43 g, 1.25 equivalents) in concentrated HCl (49.3 mL) previously cooled to −50° C. The resulting off white solid was collected after 1 hour and dried to constant weight (6.83 g, 54.6%, m.p. sintering around 143° C.). It was of sufficient purity to be used as such in the next step.

Note. A slightly higher yield (65.3%) was obtained by basifying the whole reaction mixture (to pH 13, with cold 50% NaOH) prior to the extraction of the hydrazine with ethyl acetate. The salt was then obtained by adding an excess of anhydrous HCl to an ethereal solution of the base.

NMR (DMSO-d$_6$, 200 MHz): δ6.86 (m, 3H, C$_2$H+C$_4$H+C$_6$H), 7.4 (5, 1H, C$_5$H).

Step (3) Preparation of 4-[3-Trifluoromethoxyphenylhydrazono]-1-butanol m-Trifluoromethoxyphenylhydrazine hydrochloride (6.83 g, 29.9 mmol), was dissolved in THF (83 mL) and water (83 mL). Dihydrofuran (2.1 g, 2.39 mL, 29.9 mmol, d=0.927) was added in one portion and the reaction mixture was stirred under nitrogen for 3 hours. At this point no hydrazine was present by TLC. The mixture was extracted with ether (3X) and the extracts were washed with brine, dried (MgSO$_4$) and evaporated to dryness. The residue (yellow oil, 6.94 g, 94%, mixture of E/Z isomers) was used as such in the next step.

Step (4) Preparation of 4- and 6-Trifluoromethoxytryptophol

A mixture of crude 4-[3-trifluoromethoxyphenylhydrazono]-1-butanol (6 g, 22.9 mmol) and zinc chloride (7.35 g, 53.42 mmol) in ethylene glycol (38 mL) was heated under nitrogen until homogeneous (at 85°-90° C.). The temperature was raised to 150°-160° C. for 3 hours. At this point no starting material appeared to be present by TLC (methanol-chloroform 1:9 or CH$_2$Cl$_2$—EtOAc 95:5). The hydrazone stains blue with Vaughn's reagent vs. reddish-brown for the tryptophols). The cooled reaction mixture was poured into 1N-HCl (18 mL) and extracted with ether (4×). The extracts were washed with brine, dried (MgSO$_4$) and evaporated to dryness. Flash chromatography of the residue (on silica Merck-60, using either dichloromethane-EtOAc 95:5 or toluene-EtOAc 70:30 as eluant) afforded only partial separation of the 6- from the more polar 4-isomer (brown oil, 1.8 g, 32%). Therefore the mixture of 6- and 4-substituted tryptophols (ratio ca. 2.5:1) was used in the next step.

6-isomer

NMR (DMSO-d$_6$, 400 MHz): δ2.82 (t, 2H, J=7 Hz, ArCH$_2$), 3.62 (m, 2H, CH$_2$OH), 4.61 (t, 1H, J=5.3 Hz, OH), 6.93 (d, J=8 Hz, 1H, Ar-H), 7.23 (s, 1H, Ar-H), 7.27 (s, 1H, Ar-H), 7.57 (d, 1H, Ar-H), 11.0 (broad s, 1H, NH).

MS (EI, m/z): 245 (M)$^+$, 214 (bp, M-CH$_2$OH)$^+$.

4-isomer

NMR (DMSO-d$_6$, 400 MHz): δ2.90 (t, 2H, J=7 Hz, ArCH$_2$), 3.63 (m, 2H, CH$_2$OH), 4.59 (t, 1H, J=5.2 Hz, OH), 6.89 (d, J=7.7 Hz, 1H, Ar-H), 7.08 (t, 1H, J=8 Hz, Ar-H), 7.22 (s, 1H, Ar-H), 7.34 (d, 1H, J=8 Hz, Ar-H), 11.22 (broad s, 1H, NH).

Step (5) Preparation of 1-Ethyl-1,3,4,9-tetrahydro-7-(trifluoromethoxy)pyrano-[3,4-b]indole-1-acetic Acid Methyl Ester and 1-Ethyl-1,3,4,9-tetrahydro-5-(trifluoromethoxy)pyrano-[3,4-b]indole-1-acetic Acid Methyl Ester A solution of a mixture of 4- and 6-trifluoromethoxytryptophol (1.8 g, 7.9 mmol), methyl 3-methoxy-2-pentenoate (1.7 g, 11.7 mmol) and a catalytic amount of BF$_3$.Et$_2$O (0.2 mL) in dichloromethane (35 mL) was stirred at room temperature under nitrogen for 2 hours. The solution was washed with 5% NaHCO$_3$ and brine and dried (MgSO$_4$). Removal of the solvent yielded an amber oil (3 g). Flash chromatography of the residue (silica Merck-60, light petroleum ether-ether 75:25) provided 1.19 g (42.5%) of the 7-trifluoromethoxy isomer together with 0.55 g (19.6%) of the more polar 5-isomer and 0.25 g of mixture. Total yield: 1.99 g (71%). The 7-trifluoromethoxy isomer was recrystalized from ether-light petroleum ether, m.p. 78°-82° C.

NMR (CDCl$_3$, 400 MHz): δ0.81 (t, 3H, J=7.3 Hz, CCH$_2$CH$_3$), 1.97 and 2.12 (2m, 2H, CCH$_2$CH$_3$), 2.75 (m, 2H, ArCH$_2$CH$_2$O), 2.95 (dd, 2H, CCH$_2$CO$_2$), 3.72 (s, 3H, CO$_2$CH$_3$), 3.85 and 4.02 (2m, 2H, CH$_2$CH$_2$O), 6.97

(d, J=7.5 Hz, 1H, Harom), 7.23 (s, 1H, Harom), 7.44 (d, 1H, J=8.5 Hz, Harom), 9.23 (s, 1H, NH)

MS (EI, m/z): 357 (M)+, 328 (M-C$_2$H$_5$)+, 284 (b.p.)+.

Anal. Calcd. for C$_{17}$H$_{18}$F$_3$NO$_4$: C, 57.14; H, 5.08; N, 3.92%. Found: C, 56.90; H, 5.37; N, 3.88%.

The 5-trifluoromethoxy isomer was recrystallized from ether-petroleum ether, m.p. 112°–113° C.

NMR (CDCl$_3$, 400 MHz): δ0.81 (t, 3H, J=7.3 Hz, CCH$_2$CH$_3$), 1.95 and 2.11 (2m, 2H, CCH$_2$CH$_3$), 2.94 (m, 2H, ArCH$_2$CH$_2$O), 2.96 (dd, 2H, CH$_2$CO$_2$), 3.72 (s, 3H, CO$_2$CH$_3$), 3.92 and 4.01 (2m, 2H, CCH$_2$O), 6.92 (d, J=8 Hz, 1H, Harom), 7.08 (t, 1H, J=8 Hz, Harom), 7.26 (d, J=8 Hz, 1H, Harom), 9.25 (s, 1H, NH).

MS (EI, m/z): 357 (M)+, 328 (M-C$_2$H$_5$)+, 284 (b.p.)+.

Anal. Calcd. for C$_{17}$H$_{18}$F$_3$NO$_4$: C, 57.14; H, 5.08; N, 3.92%. Found: C, 57.44; H, 5.62; N, 4.00%.

Step (6) Preparation of 1-Ethyl-1,3,4,9-tetrahydro-7-(trifluoromethoxy)pyrano-[3,4-b]indole-1-acetic Acid A solution of 1-ethyl-1,3,4,9-tetrahydro-7-(trifluoromethoxy)pyrano-[3,4-b]indole-1-acetic acid methyl ester (3 g, 8.4 mmol) in ethanol (25 mL) was treated with 10% NaOH (24 mL) and stirred overnight under nitrogen at room temperature. The ethanol was removed in vacuo and the aqueous phase was diluted with water and acidified (to pH3) with cold, concentrated HCl. The mixture was extracted with ether and the extracts were combined, washed with brine and dried (MgSO$_4$). Removal of solvent yielded the crude title compound as a yellow solid (2.8 g, 97%). It was recrystallized from ether-hexane to provide an off-white solid (1.75 g, 61%), m.p. 166°–168° C. (dec.).

IR (KBr, cm$^{-1}$): 1720 (CO).

UV (MeOH, nm): 280.5 (ε7,650), 288.5 (ε7,100).

NMR (CDCl$_3$, 400 MHz): δ0.85 (t, 3H, J=7.3 Hz, CCH$_2$CH$_3$), 2.02 and 2.10 (mm, 2H, CCH$_2$, CH$_3$), 2.81 (m, 2H, ArCH$_2$), 3.01 (dd, 2H, CCH$_2$CO$_2$), 4.05 (m, 2H, CH$_2$OH), 6.98 (d, 1H, J=8.5 Hz, Harom), 7.2 (s, 1H, Harom), 7.44 (d, J=8.5 Hz, 1H, Harom), 8.82 (s, 1H, NH).

MS (EI, m/z): 343 (M)+, 314 (M-C$_2$H$_5$)+, 284 (b.p.), 69 (CF$_3$)+.

Anal. Calcd. for C$_{16}$H$_{16}$F$_3$NO$_4$: C, 55.98; H, 4.70; N, 4.08%. Found: C, 55.81; H, 4.87; N, 4.23%.

Step (7) Preparation of 1-Ethyl-1,3,4,9-tetrahydro-5-(trifluoromethoxy)pyrano-[3,4-b]indole-1-acetic Acid A solution of 1-ethyl-1,3,4,9-tetrahydro-5-(trifluoromethoxy)pyrano[3,4-b]indole-1-acetic acid methyl ester (1 g, 2.8 mmol) in ethanol (10 mL) was treated with 10% NaOH (10 mL) and stirred overnight under nitrogen at room temperature. The ethanol was removed in vacuo and the residue was diluted with water, acidified (to pH3) with cold concentrated HCl and extracted with ether. The extracts were washed with brine and dried (MgSO$_4$). Removal of the solvent yielded the crude title compound. It was recrystallized from ether-hexane to provide a white solid (0.7 g, 73%), m.p. 158°–159° C.

IR (KBr, cm$^{-1}$): 1710 (CO).

UV (MeOH, nm): 277.5 (ε8,300).

NMR (CDCl$_3$, 400 MHz): δ0.87 (t, 3H, J=7.3 Hz, CCH$_2$CH$_3$), 2.02 and 2.12 (mm, 2H, CCH$_2$CH$_3$), 3.0 (m, 2H, ArCH$_2$CH$_2$O), 3.03 (dd, 2H, CH$_2$CO$_2$), 4.06 (m, 2H, CCH$_2$O), 6.94 (d, J=7 Hz, 1H, Harom), 7.09 (t, 1H, J=8 Hz, Harom), 7.22 (d, J=8.4 Hz, 1H, Harom), 8.9 (s, 1H, NH).

MS (EI, m/z): 343 (M)+, 314 (M-C$_2$H$_5$)+, 284 (b.p.), 69 (CF$_3$)+.

Anal. Calcd. for C$_{16}$H$_{16}$F$_3$NO$_4$: C, 55.98; H, 4.70; N, 4.08%. Found: C, 55.62; H, 4.85; N, 4.31%.

EXAMPLE 2

1-Ethyl-1,3,4,9-tetrahydro-7-(trifluoromethoxy)-pyrano-[3,4-b]indole-1-acetic Acid and 1-Ethyl-1,3,4,9-tetrahydro-5-(trifluoromethoxy)-pyrano-[3,4-b]indole-1acetic Acid Process B Step (1) Preparation of 2-[3-Trifluoromethoxyphenylhydrazono]glutaric Acid Monoethyl Ester m-Trifluoromethoxyaniline (1.77 g, 10 mmol prepared by the process of Example 1, Step 1) was added dropwise to a stirred and cooled (ice bath) mixture of concentrated HCl (2.46 mL, 29.61 mmol) and water (3.5 mL). The resulting suspension was cooled to −10° C. and treated dropwise with a solution of NaNO$_2$ (0.690 g, 10 mmol) in water (1.95 mL) taking care to keep the temperature below −5° C. When the diazotization was complete (10–15 minutes) the solution was cooled to −10° C. and added rapidly to a mechanically stirred, ice cold solution of KOH (2.23 g) in water (5.2 mL) to which have just been added ice (4.5 g) and diethyl -acetyl glutarate (2.3 g, 2.14 mL, 10 mmol, d=1.071). The deep yellow solution was stirred in an ice bath for 30 minutes, slightly acidified in the cold with 6N-HCl and extracted with ether. The extracts were washed (brine), dried (MgSO$_4$) and evaporated to yield a red oil that solidified upon standing. Flash chromatography of the residue (pre-adsorbed on silica Merck-60, dichloromethane-ethyl acetate 90:10 and 80:20) provided a small quantity of crude diester 2-[3-trifluoromethoxyphenylhydrazono]glutaric acid diethyl ester followed by the more polar monoacid title compound (1.13 g, 32.5%, red solid) as the major component.

NMR (CDCl$_3$, 200 MHz): δ1.4 (t, 3H, CH$_2$CH$_3$), 2.75 (m, 2H, CCH$_2$), 2.90 (m, 2H, CH$_2$C), 4.25 (q, 2H, CH$_2$CH$_3$), 6.8 (d, 1H, Ar-H), 7.0 (d, 1H, Ar-H), 7.1 (s, 1H, Ar-H), 7.3 (m, 1H, Ar-H), 9.5 (s, 1H, NH).

MS (EI, m/z): 348 (M)+, 274 (M-EtOH-CO)+, 246, 176 (b.p.,

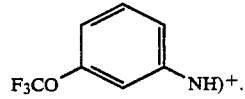

Further washing of the column with methanol gave a small quantity of the corresponding diacid 2-[3-trifluoromethoxyphenylhydrozono]glutaric acid.

Step (2) Preparation of 2-[3-Trifluoromethoxyphenylhydrazono]glutaric Acid Diethyl Ester A solution of 2-[3-trifluoromethoxyphenylhydrazono]glutaric acid mono ethyl ester (1.2 g, 3.17 mmol) in 15% ethanolic HCl (w/w, 8 mL) was gently refluxed for 4 hours. Anhydrous HCl was then bubbled through while heating (10 minutes) and the mixture was refluxed another 30 minutes. The solution was cooled, diluted with water and extracted with ether. The extracts were washed (brine and 5% NaHCO$_3$), dried (MgSO$_4$) and evaporated to dryness. Flash chromatography of the residue (on silica Merck-60, toluene-EtOAc 98:2 and 97:3) yielded the title hydrazone diesters (less polar isomer A, yellow solid, 0.661 g, 55.5%; more polar isomer B, pale yellow oil, 0.244 g, 20.5%).

Isomer A

NMR (CDCl₃, 200 MHz): δ1.30 (t, 3H, CH₂C$\underline{H_3}$), 1.39 (t, 3H, CH₂C$\underline{H_3}$), 2.68 (t, 2H, CH₂C), 2.90 (t, 2H, CH₂C), 4.16 (q, 2H, $\underline{CH_2}$CH₃), 4.3 (q, 2H, $\underline{CH_2}$CH₃), 6.8 (d, 1H, Ar-H), 7.0 (d, 1H, Ar-H), 7.05 (s, 1H, Ar-H), 7.28 (t, 1H, Ar-H).

MS (EI, m/z): 376 (M)+, 176 (b.p.

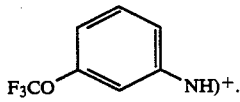

Isomer B

NMR (CDCl₃, 200 MH): δ1.25 (t, 3H, CH₂CH₃), 1.4 (t, 3H, CH₂CH₃), 2.7 (t, 2H, CH₂C), 2.88 (t, 2H, CH₂C), 4.18 (q, 2H, CH₂CH₃), 4.32 (q, 2H, CH₂CH₃), 6.82 (d, 1H, Ar-H), 7.14 (d, 1H, Ar-H), 7.15 (s, 1H, Ar-H), 7.30 (t, 1H, Ar-H).

MS (EI, m/z): 376 (M)+, 330 (M-CO)+, 302, 274, 200, 176 (b.p.,

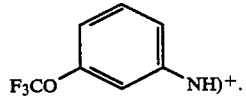

Further washing of the column gave a small quantity of the more polar mixture of 4- and 6-trifluoromethoxy-2-carboethoxy-3-indoleacetic acid ethyl ester.

Step (3) Preparation of 4- and 6-Trifluoromethoxy-2-carboethoxy-3-indoleacetic Acid Ethyl Ester A solution of 2-[3-trifluoromethoxyphenylhydrazono]glutaric acid diethyl ester (isomer A, 0.608 g, 1.61 mmol) in glacial acetic acid (4 mL) containing BF₃·etherate (0.24 mL) was stirred at reflux under nitrogen for 30 minutes. The solution was diluted with water and extracted with ether. The extracts were washed with 5% NaHCO₃ and brine, dried (MgSO₄) and evaporated to dryness. Flash chromatography of the residue (on silica Merck-60, toluene-EtOAc 95:5) yielded the mixture of title compounds as a white solid (0.060 g, 10.4%), m.p. 110°–112° C.

NMR (CDCl₃, 200 MHz): δ1.25 (t, J=7 Hz, 3H, CH₃), 1.41 (t, J=7 Hz, 3H, CH₃), 4.14 (s, 2H, CH₂CO₂), 4.16 (q, J=7 Hz, 2H, CH₂), 4.42 (q, J=7 Hz, 2H, CH₂), 7.04 (d, J=8 Hz, 1H, Ar-H), 7.26 (s, 1H, Ar-H), 7.65 (d, J=8.5 Hz, 1H, Ar-H), 9.0 (broad, 1H, NH).

MS (EI, m/z): 359 (M)+, 313, 286, 240 (b.p.).

Step (4) Preparation of 4- and 6-Trifluoromethoxy-2-carboxy-3-indoleacetic Acid

A solution of the mixture of 4- and 6-trifluoromethoxy-2-carboethoxy-3-indoleacetic acid ethyl ester (0.218 g, 0.6 mmol) in ethanol (2.5 mL) was treated with 2.5N-NaOH (1.39 mL, 3.47 mmol) and stirred at reflux under nitrogen for 30 minutes. The solvent was evaporated and the residue was diluted with water and extracted with ether. The aqueous layer was acidified in the cold with 2N-HCl (to pH 3) and extracted with ethyl acetate. The extracts were washed (brine) and dried (MgSO₄) to yield a mixture of 4- and 6-trifluoromethoxy-2-carboxy-3-indoleacetic acid as a yellow solid (0.152 g, 82.6%). This crude material (mixture of 4 and 6 isomers) was used as such in the next step.

Step (5) Preparation of 4- and 6-Trifluoromethoxy-2-carboxy-3-indoleacetic Acid Ethyl Ester A solution of the crude mixture of 4- and 6-trifluoromethoxy-2-carboxy-3-indoleacetic acid (0.280 g, 0.59 mmol) in 0.5% ethanolic HCl (1.7 mL) was gently refluxed under nitrogen for 60 minutes. Removal of the solvent in vacuo yielded the crude mixture of 4- and 6-trifluoromethoxy-2-carboxy-3-indoleacetic acid ethyl ester as a yellow oil that solidified upon standing (0.170 g, 86.7%). This crude material (mixture of 4 and 6 isomers) was used as such in the next step.

Step (6) Preparation of 4- and 6-Trifluoromethoxy-3-indoleacetic Acid Ethyl Ester A crude mixture of the 4- and 6-trifluoromethoxy-2-carboxy-3-indoleacetic acid ethyl ester (0.160 g, 0.48 mmole) in quinoline (3 mL) containing a catalytical amount of 39KAF [0.030 g, prepared according to Conner et al, J. Amer. Chem. Soc., 54, 1142 (1932)] was stirred under nitrogen at 200° C. (oil bath temperature) until the evolution of CO₂ ceased (about 20 minutes). Upon cooling the dark mixture was diluted with ether, filtered (glass wool) to remove the catalyst and extracted with 1N HCl to remove as much quinoline as possible. The organic layer was then washed with brine, 5% NaHCO₃ and again brine, dried (MgSO₄) and evaporated to dryness. Flash chromatography of the residue (on silica Merck-60, toluene-EtOAc 95:5) afforded only partial separation of the 6- from the more polar 4- isomer. Therefore the mixture of the 6- and 4-trifluoromethoxy-3-indoleacetic acid ethyl ester (ratio about 3:1) was used in the next step (0.097 g, 70%, oil).

Step (7) Preparation of 4- and 6-(Trifluoromethoxy)-tryptophol

A solution of the mixture of 4- and 6-trifluoromethoxy-3-indoleacetic acid ethyl ester (0.090 g, 0.313 mmol) in dry THF (5 mL, ex-CaH₂) was treated with LAH (0.0238 g, 6.27 mmol) and then stirred under nitrogen at room temperature for 30 minutes.

The mixture was diluted with THF and treated sequentially with water (0.025 mL), 1N-NaOH (0.025 mL), water (0.075 mL) and Na₂SO₄ (0.3 g).

Removal of the solvent yielded a residue (0.075 g) identical (in two different solvent systems) with the mixture of 4- and 6-trifluoromethoxy tryptophols obtained in Example 1, Step 4.

This mixture of 4- and 6-trifluoromethoxy tryptophols was treated as in Process A, Example 1, Step 5 to Step 7 to produce
1-ethyl-1,3,4,9-tetrahydro-7-(trifluoromethxy)-pyrano[3,4-b]indole-1-acetic acid; and
1-ethyl-1,3,4,9-tetrahydro-5-(trifluoromethoxy)-pyrano[3,4-b]indole-1-acetic acid.

EXAMPLE 3

1-Ethyl-1,3,4,9-tetrahydro-6-(trifluoromethoxy)-pyrano[3,4-b]indole-1-acetic Acid Process A Step (1) Preparation of 4-Trifluoromethoxyphenylhydrazine Hydrochloride A suspension of p-trifluoromethoxyaniline (5.0 g, 28 mmol) in 33 mL of concentrated HCl was diazotized at 0°–10° C. with a solution of sodium nitrite (2.0 g, 29 mmol) in H₂O (17 mL). After stirring for 15 minutes at −5° C., the turbid solution was made clear by the addition of a few drops of water. A solution of stannous chloride (12.6 g, 56 mmol) in concentrated HCl (11 mL) was added in one portion. The mixture was stirred for 3 hours (with the ice bath removed after 1 hour), basified with 50% NaOH and extracted with EtOAc (2×). The organic phase was washed with 1N NaOH and brine, dried (KOH pellets) and acidified with anhydrous HCl. The precipitate was filtered and dried to give the title product as the white solid hydrochloride salt [4.83 g, mp 231° C. (dec.)]. A second crop was obtained by concentration of the mother liquors (0.62 g). Combined yield 5.45 g (85%).

$^1$H NMR (DMSO-d$_6$, 400 MHz): δ7.04 (d, 2H, J=8.5 Hz, Ar-H), 7.29 (d, 2H, J=8.5 Hz, Ar-H), 8.52 (broad, 1H, NHNH$_2$), 10.32 (broad, 3H, NHNH$_3^+$)

Anal. Calcd. for C$_7$H$_7$F$_3$N$_2$O.HCl: C, 36.78; H, 3.53; N, 12.25. Found C, 36.72; H, 3.76; N, 12.02.

Step (2) Preparation of 4-(4-Trifluoromethoxyphenylhydrazono)-1-butanol

A solution of 4-trifluoromethoxyphenylhydrazine hydrochloride (5.4 g, 23.7 mmol), and 2,3-dihydrofuran (1.65 g, 23.7 mmol) in 75 mL of THF-H$_2$O (1:1, v/v) was stirred at room temperature for 2 hours. The reaction mixture was then partitioned between Et$_2$O and water. The organic phase was washed with brine and dried. Removal of the solvent afforded fairly pure product as a yellow oil (5.67 g, 92%, mixture of E/Z isomers).

$^1$H NMR (CDCl$_3$, 400 MHz): δ1.8 (m, 2H, CCH$_2$C), 3.85 (m, 2H, CH$_2$CH$_2$O), 6.9-7.2 (m, 5H, Ar-H+CCH=N)

MS (EI, m/z): 262 (M)$^+$, 176 (b.p.,

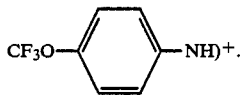

Step (3) Preparation of 5-Trifluoromethoxytryptophol

A mixture of 4-(4-trifluoromethoxyphenylhydrazono)-1-butanol (5.6 g, 21.4 mmol) and zinc chloride (5.8 g, 42.8 mmol) in ethylene glycol (25 mL) was heated under nitrogen at 160° C. for 3 hours. The cooled reaction mixture was partitioned between Et$_2$O and H$_2$O. The organic phase was washed with 1N HCl and brine and dried (Na$_2$SO$_4$). Removal of the solvent under reduced pressure gave fairly pure crude product (4.7 g, 90%, brown oil). It was used in the next step without further purification.

$^1$H NMR (CDCl$_3$, 400 MHz): δ1.65 (broad, 1H, OH), 3.01 (t, 2H, J=6 Hz, ArCH$_2$C), 3.92 (t, 2H, J=6 Hz, CCH$_2$O), 7.08 (dd, 1H, J=8.5 Hz, Ar-H), 7.17 (d, 1H, J=2 Hz, Ar-H), 7.34 (d, 1H, J=8.5 Hz, Ar-H), 7.46 (s, 1H, Ar-H), 8.15 (broad, 1H, NH).

MS (EI, m/z): 245 (M)$^+$, 214 (b.p., M-CH$_2$OH)$^+$, 145 (214-CF$_3$)$^+$.

Step (4) Preparation of 1-Ethyl-1,3,4,9-tetrahydro-6-(trifluoromethoxy)pyrano[3,4-b]indole-1-acetic Acid Methyl Ester A solution of 5-trifluoromethoxytryptophol (4.7 g, 19.1 mmol), methyl 3-methoxy-2-pentenoate (3.3 g, 23 mmol) and a catalytic amount of BF$_3$.Et$_2$O in dry methylene chloride (20 mL) was stirred overnight at ambient temperature. The reaction mixture was diluted with an equal portion of methylene chloride, washed with 5% NaHCO$_3$ (50 mL) and brine (50 mL) and dried (Na$_2$SO$_4$). Removal of the solvent afforded 7.2 g of an orange oil. The crude product was purified by flash chromatography (silica Merck-60, chloroform-methanol 95:5) to give the title compound (6.25 g, 92%, amber oil).

$^1$H NMR (CDCl$_3$, 400 MHz): δ0.81 (t, 3H, J=7 Hz, CH$_2$CH$_3$), 1.98 and 2.13 (2m, 2H, CCH$_2$CH$_3$), 2.75 (m, 2H, Ar-CH$_2$C), 2.95 (dd, 2H, CCH$_2$COO), 3.72 (s, 3H, CO$_2$CH$_3$), 3.83 and 4.05 (2m, 2H, CCH$_2$O), 7.03 (d, 1H, Ar-H), 7.31 (d, 1H, J=8.7 Hz, Ar-H), 7.32 (s, 1H, Ar-H), 9.2 (s, 1H, NH).

MS (EI, m/z): 357 (M)$^+$, 328 (M-C$_2$H$_5$)$^+$, 284 (b.p.).

Step (5) Preparation of 1-Ethyl-1,3,4,9-tetrahydro-6-(trifluoromethoxy)pyrano[3,4-b]indole-1-acetic Acid A mixture of 1-ethyl-1,3,4,9-tetrahydro-6-(trifluoromethoxy)pyrano[3,4-b]indole-1-acetic acid methyl ester (6.2 g, 17.4 mmol) in ethanol (80 mL) and 2.5N NaOH (24 mL) was stirred at ambient temperature under nitrogen for 3 hours. The ethanol was removed in vacuo and the residue was diluted with H$_2$O (70 mL) and washed with ether. The aqueous phase was acidified (to pH3) with 2N-HCl and extracted with Et$_2$O. The extract was washed with brine and dried (Na$_2$SO$_4$). Removal of the solvent afforded the crude product (5.2 g, amber oil). Crystallization from Et$_2$O-hexane gave 3.43 g of the pure title compound (mp 148° C., white solid). A second crop was obtained from the mother liquor (0.54 g, mp 148° C., light brown solid). The combined yield was 67%.

$^1$H NMR (CDCl$_3$, 400 MHz): δ0.87 (t, 3H, J=7.4 Hz, CH$_2$CH$_3$), 2.02 and 2.12 (2m, 2H, CCH$_2$CH$_3$), 2.82 (m, 2H, ArCH$_2$C), 3.03 (dd, 2H, CCH$_2$CO$_2$), 4.06 (m, 2H, ArCH$_2$CH$_2$O), 7.04 (d, 1H, J=8.5 Hz, Ar-H), 7.29 (d, 1H, J=8.5 Hz, Ar-H), 7.34 (s, 1H, Ar-H), 8.7 (s, 1H, NH).

IR (KBr, cm$^{-1}$): 1695 (CO).

MS (CI, m/z): 344 (M+H)$^+$, 343 (M)$^+$, 314 (M-C$_2$H$_5$)$^+$, 284 (M-CH$_2$COOH)$^+$.

Anal. Calcd. for C$_{16}$H$_{16}$F$_3$NO$_4$: C, 55.98; H, 4.70; N, 4.08. Found: C, 55.88; H, 4.98; N, 4.00.

EXAMPLE 4

1-Ethyl-1,3,4,9-tetrahydro-8-(trifluoromethoxy)-pyrano[3,4-b]indole-1-acetic Acid Process A Step (1) Preparation of 2-Trifluoromethoxyphenylhydrazine Hydrochloride A solution of o-trifluoromethoxyaniline (1.77 g, 10 mmol) in cold, concentrated HCl (11.6 mL) was diazotized at −5° C. (internal temperature) with a solution of NaNO$_2$ (0.69 g, 10 mmol) in water (11 mL). After 15-20 minutes the mixture was treated portionwise with a cold (0° C.) solution of tin (II)chloride dihydrate (4.5 g, 20 mmol) in concentrated HCl (4 mL). Stirring was continued for another 3 hours with the ice bath warming to room temperature after one hour. The suspension was recooled, basified with 50% NaOH (to pH 14) and extracted with ether. The extracts were washed with 1N NaOH, water and brine, dried (MgSO$_4$) and acidified with an excess of ethereal HCl. Removal of the solvent in vacuo yielded the title compound as an off-white solid (2 g, 88%). It was used without further purification.

NMR (DMSO-d$_6$, 400 MHz): δ7.03 (m, 1H, ArH), 7.18 (d, J=7.5 Hz, 1H, ArH), 7.34 (m, 2H, ArH), 8.40 (s, 1H, NH).

MS (EI, m/z): 197 (M)$^+$, 77 (b.p.).

Step (2) Preparation of 4-(2-Trifluoromethoxyphenylhydrazono)-1-butanol

A solution of o-trifluoromethoxyphenylhydrazine hydrochloride (2 g, 8.77 mmol), and 2,3-dihydrofuran (0.614 g, 0.660 mL, 8.77 mmol, d=0.927) in a 1:1 (v/v) mixture of THF and water (30 mL) was stirred at room temperature for 1.5 hours under nitrogen. No hydrazine was present at this point by TLC. The mixture was extracted with ether and the ether extracts were washed with brine, dried (MgSO$_4$) and evaporated to dryness. The residue (pale yellow oil, 2.2 g, 95.7%, mixture of E/Z isomers) was used as such in the next step.

MS (EI, m/z): 262 (b.p., M)$^+$, 218 (M-CH$_2$O)$^+$, 176 (M-N=CHCH$_2$CH$_2$CH$_2$OH)$^+$.

Step (3) Preparation of 7-Trifluoromethoxytryptophol

A mixture of crude 4-(2-trifluoromethoxyphenylhydrazono)-1-butanol (2.2 g, 8.4 mmol) and zinc chloride (2.28 g, 16.8 mmol) in ethyleneglycol (10 mL) was heated under nitrogen at 90° C. until homogeneous. The temperature was then raised to 160° C. for 3 hours. The cooled reaction mixture was poured into 1N-HCl and extracted with ether. The extracts were washed with brine, dried (MgSO$_4$) and evaporated to dryness. Flash chromatography of the residue (on silica Merck-60, eluant: CHCl$_3$—CH$_3$OH 95:5) afforded 0.980 g (48%) of the desired product.

NMR (CDCl$_3$, 400 MHz): $\delta$3.03 (t, J=6.3 Hz, 2H, ArCH$_2$), 3.91 (q, J=6.2 Hz, 2H, CH$_2$OH), 7.1 (m, 3H, ArH), 7.57 (m, 1H, ArH), 8.27 (broad, 1H, NH).

MS (EI, m/z): 245 (M)$^+$, 214 (M-CH$_3$O)$^+$, 194, 128 (b.p.).

Step (4) Preparation of 1-Ethyl-1,3,4,9-tetrahydro-8-(trifluoromethoxy)pyrano[3,4-b]indole-1-acetic Acid Methyl Ester A solution of 7-trifluoromethoxytryptophol (0.98 g, 4 mmol), methyl 3-methoxy-2-pentenoate (0.72 g, 4 mmol) and a catalytic amount of boron trifluoride etherate in dichloromethane (18 mL) was stirred at room temperature for 1.5 hours. The solution was diluted with dichloromethane and washed with 5% NaHCO$_3$ and brine. The extracts were dried (MgSO$_4$) and evaporated to dryness. Flash chromatography of the residue (silica Merck-60, CHCl$_3$) provided 1.06 g (75%) of the pure product as a light yellow oil.

NMR (CDCl$_3$, 400 MHz): $\delta$0.82 (t, J=7.4 Hz, 3H, CCH$_3$), 2.00 and 2.16 (2m, 2H, CCH$_2$C), 2.80 (m, 2H, ArCH$_2$C), 2.96 (dd, J=16.57 Hz, 2H, CCH$_2$COO), 3.72 (s, 3H, COOCH$_3$), 3.95 and 4.05 (2m, 2H, CCH$_2$O), 7.06 (d, J=4.9 Hz, 2H, ArH), 7.42 (m, 1H, ArH), 9.28 (broad s, 1H, NH).

MS (EI, m/z): 357 (M)$^+$, 328 (M-C$_2$H$_5$)$^+$, 284 (b.p.).

Step (5) Preparation of 1-Ethyl-1,3,4,9-tetrahydro-8-(trifluoromethoxy)pyrano[3,4-b]indole-1-acetic Acid A solution of 1-ethyl-1,3,4,9-tetrahydro-8-(trifluoromethoxy)-pyrano[3,4-b]indole-1-acetic acid methyl ester (1.5 g, 4.2 mmol) in ethanol (20 mL) containing 2.5N NaOH (6 mL) was stirred for 3 hours at room temperature (reaction followed by TLC). The ethanol was removed in vacuo and the residue was diluted with water and washed with ether. The aqueous phase was acidified (to pH3) with cold, concentrated HCl and extracted with ether. The extracts were washed with brine, dried (MgSO$_4$) and evaporated to dryness. The crude product (1.4 g) was recrystallized from ether-hexane to provide a white solid (0.975 g, 68%, mp 142°-143.5° C.).

UV (MeOH, nm): $\lambda$278.5 ($\epsilon$8,100), 227 ($\epsilon$7,800).

NMR (CDCl$_3$, 400 MHz): $\delta$0.86 (t, J=7.4 Hz, 3H, CCH$_3$), 2.05 and 2.15 (2m, 2H, CCH$_2$C), 2.83 (m, 2H, ArCH$_2$), 3.05 (dd, J=16.5 Hz, 2H, CCH$_2$COO), 4.08 (m, 2H, CCH$_2$O), 7.07 (d, 2H, ArH), 7.42 (m, 1H, ArH), 8.94 (s, 1H, NH).

MS (EI, m/z): 343 (M)$^+$, 314 (M-C$_2$H$_5$)$^+$, 284 (b.p.).

Anal. Calcd. for C$_{16}$H$_{16}$F$_3$NO$_4$: C, 55.98; H, 4.70; N, 4.08. Found: C, 55.84; H, 4.85; N, 4.02.

EXAMPLE 5

1-Ethyl-1,3,4,9-tetrahydro-7-(trifluoromethoxy)-pyrano[3,4-b]indole-1-acetic Acid 3-Oxo-1-isobenzofuranyl Ester Step (1) Preparation of 3-Bromophthalide A mixture of phthalide (7.5 g, 56 mmol) and N-bromosuccinimide (10 g, 55.5 mmol) in CCl$_4$ (150 mL) was heated at reflux for 3 hours (reaction checked by TLC). The mixture was filtered hot and the filtrate was evaporated to dryness to yield the crude title compound (11.15 g, 97%). It was used as such in the next step.

Step (2) Preparation of 1-Ethyl-1,3,4,9-tetrahydro-7-(trifluoromethoxy)pyrano[3,4-b]indole-1-acetic Acid 3-Oxo-1-isobenzofuranyl Ester A solution of 1-ethyl-1,3,4,9-tetrahydro-7-(trifluoromethoxy)pyrano[3,4-b]indole-1-acetic acid (0.650 g, 1.89 mmol, prepared according to the procedure of Example 1), 3-bromophthalid (0.402 g, 1.89 mmol) and TEA (0.382 g, 3.79 mmol) in dry THF (60 mL) was refluxed for 4 hours. The solvent was evaporated and the residue was partitioned between water and ether. The extracts were washed with 5% NaHCO$_3$ and brine, dried (MgSO$_4$) and evaporated to dryness. Flash chromatography of the residue (on silica Merck-60, eluant: CHCl$_3$) provided 0.670 g (74.6%) of the pure product (as a mixture of diastereomers) which was recrystallized from ether-hexane, m.p. 150° C. (softening starts at 124° C.).

NMR (CDCl$_3$, 400 MHz): $\delta$0.83 and 0.85 (2 overlapping triplets, J=7.3 Hz, 3H, CCH$_3$), 2.02 and 2.13 (2m, 2H, CCH$_2$C), 2.82 (m, 2H, ArCH$_2$), 3.04 (dd, J=16.3 Hz, 2H, CCH$_2$COO), 3.93 and 4.02 (2m, 2H, CCH$_2$O), 6.99 (d, J=8.5 Hz, 1H, ArH), 7.22 (m, 1H, ArH), 7.42 (m, 3H, ArH), 7.65 (m, 2H, ArH), 7.89 (m, 1H, ArH), 8.68 and 8.83 (2s, NH).

MS (EI, m/z): 475 (M)$^+$, 446 (M-C$_2$H$_5$)$^+$, 284, 133 (b.p.).

Anal. Calcd. for C$_{24}$H$_{20}$F$_3$NO$_6$: C, 60.63; H, 4.20; N, 2.94. Found: C, 60.40; H, 4.33; N, 3.26.

We claim:

1. The compound 1-ethyl-1,3,4,9-tetrahydro-7-(trifluoromethoxy)pyrano[3,4-b]indole-1-acetic acid 3-oxo-1-isobenzofuranyl ester.

* * * * *